United States Patent
Sterin et al.

(10) Patent No.: US 7,750,171 B2
(45) Date of Patent: *Jul. 6, 2010

(54) CATALYST ASSEMBLY FOR HYDROSILYLATION, PROCESS FOR PREPARING IT AND SILICONE COMPOSITIONS INCORPORATING IT

(75) Inventors: Sébastien Sterin, Lyons (FR); Rémi Thiria, Lyons (FR)

(73) Assignee: Bluestar Silicones France, Lyons (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/146,974

(22) Filed: Jun. 26, 2008

(65) Prior Publication Data

US 2008/0262170 A1 Oct. 23, 2008

Related U.S. Application Data

(63) Continuation of application No. 10/512,977, filed as application No. PCT/FR03/01305 on Apr. 24, 2003, now abandoned.

(30) Foreign Application Priority Data

Apr. 29, 2002 (FR) .................................. 02 05380
Dec. 2, 2002 (FR) .................................. 02 15161

(51) Int. Cl.
- *C07F 9/02* (2006.01)
- *C07F 9/06* (2006.01)
- *C08K 5/53* (2006.01)
- *C08K 5/51* (2006.01)
- *C08G 77/30* (2006.01)
- *C08G 77/00* (2006.01)

(52) U.S. Cl. .................. 556/13; 524/135; 524/148; 528/15; 528/31

(58) Field of Classification Search ............ 528/12, 528/15, 863, 866
See application file for complete search history.

(56) References Cited

U.S. PATENT DOCUMENTS

| | | | |
|---|---|---|---|
| 3,445,420 A | | 5/1969 | Kookootsedes et al. |
| 3,715,334 A | * | 2/1973 | Karstedt ..................... 528/15 |
| 3,825,629 A | * | 7/1974 | Hofer ......................... 558/156 |
| 4,108,833 A | * | 8/1978 | Hatanaka et al. .............. 528/31 |
| 4,184,006 A | | 1/1980 | Hockemeyer et al. |
| 4,394,317 A | | 7/1983 | McAfee et al. |
| 4,645,815 A | * | 2/1987 | Lewis .......................... 528/15 |
| 4,687,870 A | | 8/1987 | Cavezzan |
| 4,699,813 A | | 10/1987 | Cavezzan |
| 4,870,115 A | * | 9/1989 | Itoh et al. .................... 521/134 |
| 4,931,485 A | * | 6/1990 | Inoue et al. .................. 521/154 |
| 5,109,043 A | * | 4/1992 | Bohshar et al. .............. 524/126 |
| 5,125,998 A | | 6/1992 | Jones et al. |
| 5,158,992 A | * | 10/1992 | Caselli et al. ................ 523/207 |
| 5,326,803 A | * | 7/1994 | Avakian et al. .............. 524/120 |
| 5,380,812 A | * | 1/1995 | Lutz et al. ....................... 528/15 |
| 5,385,961 A | * | 1/1995 | Avakian et al. .............. 523/213 |
| 5,696,210 A | * | 12/1997 | King et al. .................... 525/478 |
| 6,187,890 B1 | * | 2/2001 | Fehn et al. ....................... 528/15 |
| 6,300,455 B1 | * | 10/2001 | Haselhorst et al. ............ 528/31 |
| 6,346,562 B1 | * | 2/2002 | Haselhorst et al. .......... 524/106 |
| 6,455,617 B1 | | 9/2002 | Gay et al. |
| 6,518,453 B1 | * | 2/2003 | Sutoris et al. ................ 560/205 |
| 6,593,485 B1 | * | 7/2003 | Stoll et al. ..................... 558/71 |
| 6,803,440 B2 | * | 10/2004 | Marko et al. ................... 528/14 |
| 2002/0103308 A1 | * | 8/2002 | Chorvath et al. ............. 525/446 |
| 2003/0097017 A1 | * | 5/2003 | Sutoris et al. .................. 560/4 |
| 2004/0097663 A1 | * | 5/2004 | Deforth et al. .............. 525/474 |
| 2004/0116561 A1 | * | 6/2004 | Ikeno et al. .................. 524/115 |
| 2006/0047097 A1 | * | 3/2006 | Tanaka et al. ................. 528/15 |
| 2006/0128881 A1 | * | 6/2006 | George et al. ............... 524/588 |

FOREIGN PATENT DOCUMENTS

| | | | |
|---|---|---|---|
| DE | 197 57 221 | * | 6/1999 |
| DE | 197 57 221 A1 | | 6/1999 |
| WO | WO 99/33911 A1 | | 7/1999 |
| WO | WO 02/06381 A1 | | 1/2002 |

OTHER PUBLICATIONS

MSDS for Irgafos 168, 53 pages, 2001.*
Manojilović-Muir, L., et al., "Platinum (II) Complexes with Ligands (RO)$_2$PCH$_2$P(OR)$_2$(R=Me,Et,Ph, or C$_6$H$_4$Me-4); Crystal Structure of cis,cis-[Pt$_2$Me$_4${μ-EtO)$_2$PCH$_2$P(OEt)$_2$}$_2$]," *Journal of the Chemical Society, Dalton Transactions*, 1987, pp. 2117-2124, No. 9, Chemical Society, Letchworth, GB.
International Search Report issued in corresponding PCT/FR03/01305, mailed Mar. 17, 2004, EPO, Rijswijk, NL, in English.
Official Action issued by, U.S. Appl. No. 10/512,977, Dec. 26, 2007, 22 pages, U. S. Patent and Trademark Office.

* cited by examiner

*Primary Examiner*—Randy Gulakowski
*Assistant Examiner*—Robert Loewe
(74) *Attorney, Agent, or Firm*—Buchanan Ingersoll & Rooney PC

(57) ABSTRACT

Process for preparing catalyst assemblies by mixing a metal catalyst capable of catalyzing a hydrosilylation reaction and an organophosphorus inhibitor of the formula (I)

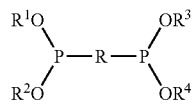

or of formula (VIII) P(OR)$_3$, either by mixing the inhibitor into a solution of catalyst in an unsaturated silane or siloxane or by mixing the inhibitor into a gum or oil at a temperature greater than the melting temperature or softening temperature of the organophosphorus compound, then mixing the catalyst. Catalyst assemblies, process for preparing one-component silicone compositions, and resultant compositions.

39 Claims, No Drawings

CATALYST ASSEMBLY FOR HYDROSILYLATION, PROCESS FOR PREPARING IT AND SILICONE COMPOSITIONS INCORPORATING IT

CROSS-REFERENCE TO RELATED APPLICATIONS

This application is a continuation of copending U.S. patent application Ser. No. 10/512,977, filed Aug. 30, 2005, which is the U.S. national phase of International Application No. PCT/FR03/01305, filed Apr. 24, 2003 and claiming priority of Application No. 02/05380 filed in France on Apr. 29, 2002 and also claiming priority of Application No. 02/15161, filed on Dec. 2, 2002 in France, all of said applications being expressly incorporated by reference herein in their entireties and relied upon.

The invention relates to new inhibitors of catalysts of hydrosilylation reactions that involve polyorganosiloxanes (POS) bearing Si—H units and POS bearing ethylenic and/or acetylenic unsaturation(s), referred to hereinafter as POS bearing Si-[ethylenic or acetylenic unsaturation] units, and to the catalyst assemblies obtained from the mixture of these inhibitors and catalysts. The invention also pertains to one-component silicone compositions which crosslink by way of hydrosilylation reactions and comprise such an inhibitor or catalyst assembly.

The invention likewise relates to particular methods of employing hydrosilylation catalyst inhibitors, to processes for preparing mixtures of inhibitors and catalysts, to processes for preparing one-component silicone compositions and to the compositions obtainable by employing these processes.

Hydrosilylation reactions allowing silicones to crosslink are conventionally catalysed by platinum catalysts (U.S. Pat. No. 2,823,218, U.S. Pat. No. 2,970,150). In practice the majority of industrial hydrosilylation reactions have to date been catalysed by Karstedt solution, which is composed of complexes of platinum in oxidation state 0 (U.S. Pat. No. 3,775,452 and U.S. Pat. No. 3,715,334). The ideal general formula of the Karstedt complex is $Pt_2$(tetramethyldivinylsiloxane)$_3$:

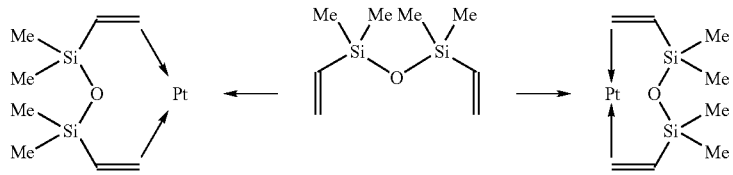

where Me represents methyl.

The Karstedt complex can be prepared by contacting 1,3-divinyl-tetramethyldisiloxane with chloroplatinic acid ($H_2PtCl_6$), in the presence of $NaHCO_3$ and an aqueous-alcoholic solvent (e.g. isopropanol).

The very high catalytic activity of this type of catalyst, even at room temperature, is a major drawback in the context of its use in polyaddition HTV elastomers, since the crosslinking of the elastomer begins as soon as the components are contacted with one another.

More stable metallic Pt/carbene complexes have been proposed. Thus, FR-A-2 801 887 discloses metal complexes useful as hydrosilylation catalysts, of formula:

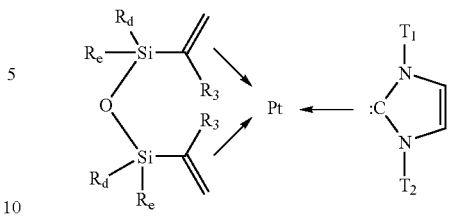

in which:

$R_3$ represents a hydrogen atom; a $(C_1\text{-}C_8)$alkyl group; or a $(C_3\text{-}C_8)$cycloalkyl group optionally substituted by $(C_1\text{-}C_4)$ alkyl;

$T_1$ and $T_2$ are identical and represent $(C_1\text{-}C_8)$alkyl or $(C_3\text{-}C_8)$ cycloalkyl;

$R_d$ and $R_e$ are identical and represent $(C_1\text{-}C_8)$alkyl or $(C_3\text{-}C_8)$ cycloalkyl;

(preferably $T_1=T_2=R_d=R_e=$methyl).

Conventionally, in order to increase the room-temperature storage stability (pot life) of one-component silicone compositions which can be crosslinked by hydrosilylation reaction, use is made of crosslinking inhibitors which act by masking the activity of the catalyst at room temperature. The activity of the catalyst is restored when the temperature is raised. Organophosphorus compounds have been proposed.

Thus U.S. Pat. No. 3,188,300 describes the use of various phosphine or phosphite ligands of formula:

in which $R^1$, $R^2$ and $R^3$, which are identical or different, are alkyl, aryl, aralkyl, alkaryl, alkoxy, aryloxy, aralkoxy or alkaryloxy radicals.

U.S. Pat. No. 5,380,812 proposes di- and trihydrocarbylphosphines, di- and trihydrocarbylphosphine oxides, di- and triorganophosphites of formula

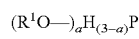

and phospholene oxides. In the above formula $R^1$ is a substituted or unsubstituted monovalent hydrocarbon radical, for example alkyl, aralkyl or alkaryl, and a is 2 or 3.

Mention may also be made of U.S. Pat. No. 4,593,084, U.S. Pat. No. 5,654,455 and U.S. Pat. No. 6,300,455. The latter describes phosphite ligands of formula $P(OR)_3$ in which R is a $C_7\text{-}C_{31}$ radical or an alkylaryl radical. Preferred ligands are of formula:

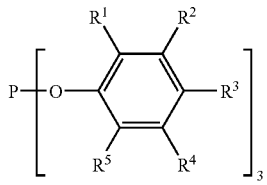

The phosphines make it possible to inhibit the platinum instantaneously, but their affinity for platinum is such that the catalyst system finally obtained exhibits mediocre reactivity. Phosphites present a more advantageous trade-off between inhibition and reactivity.

Beyond the selection of an inhibitor/catalyst pairing, the properties of the catalyst systems may depend on the conditions under which they are employed and on the dispersion of the inhibitor/catalyst pairing in the silicone material.

In U.S. Pat. No. 6,300,455 the organophosphorus inhibitor (compound d) is added to the vinylsilicone oil (compound a) before the hydrosilylation catalyst (compound c) is added, and then the polyhydrosiloxane (compound b) is added in its turn.

However, generally speaking, organophosphorus compounds are soluble only sparingly, if at all, in silicone oils, which tends to give rise to poor dispersion of these compounds. The result is that the complexation of the platinum, and hence its inhibition, may take a long time to be obtained with such a method, which therefore opens up the risk of a non-optimum homogeneity and of premature crosslinking of the end composition.

It would be advantageous to have inhibitors which allow a high inhibitory power to be combined with an effective catalytic activity, and which make it possible to prepare one-component compositions having a satisfactory pot life, e.g. of from 1 day to several months. It would also be advantageous to have methods of employing these inhibitors/catalysts which are highly effective.

The objective of the present invention is therefore to respond to this need by providing new inhibitors and more particularly a new catalyst assembly comprising a catalyst and an inhibitor, the catalytic activity being inhibited (undetectable) at room temperature.

Another objective of the invention is to provide methods of employing inhibitor/catalyst pairings which make it possible to ensure, under the best of conditions, catalyst/inhibitor coupling and/or dispersion of the catalyst, the inhibitor and the catalyst assemblies in a silicone composition.

Yet another objective of the invention is to provide catalyst assemblies exhibiting enhanced ease of use, particularly for their mixing with silicone compositions.

Another objective, additionally, of the invention is to provide a silicone composition which is crosslinkable by hydrosilylation and comprises as catalyst a catalyst assembly of this kind having inhibited activity at room temperature, so as to make it possible to produce one-component compositions, comprising the catalyst and compounds capable of reacting at high temperature by way of hydrosilylation of unsaturated units (e.g. SiH POS/Si-alkenyl POS), while being stable at room temperature for long periods (e.g. 1 day to several months).

The present invention accordingly provides a catalyst composition or assembly comprising a metal catalyst capable of catalysing a hydrosilylation reaction and an inhibitor of the following formula (I):

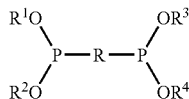

in which:

R, $R^1$, $R^2$, $R^3$ and $R^4$, which are identical or different, represent a linear, branched or cyclic alkyl radical or an aryl radical which is substituted or unsubstituted, especially:
  a linear or branched alkyl radical having particularly 2 to 30 carbon (C) atoms, preferably 2 to 12 C,
  an alkyl radical containing one or more rings, especially 1 or 2, it being possible in particular for one ring to have 4 to 14 C, preferably 5 to 8 C, or
  an aryl or alkylaryl radical containing one or more fused or unfused aromatic rings, especially 1 or 2 rings, it being possible for one ring to contain 4 to 14 C, preferably 6 to 8 C, which is or are optionally substituted by 1 or more, especially 1 to 2, linear or branched alkyl(s), especially having 1 to 12 C, preferably 4 to 12 C, the inhibitor in the composition or assembly inhibiting the catalytic action of the catalyst. In particular the catalytic action is inhibited at room temperature but may be restored by heating (e.g. between 50 and 200° C., more particularly between 100 and 150° C.). In the composition or assembly, inhibitor and catalyst are complexed. Without wishing to be bound by a specific theory, it is thought that the complexation results from interactions between P and Pt, as will be illustrated later on. In the present invention the term "inhibition" embraces what is known as complete inhibition, owing to the incorporation of a sufficient amount of inhibitor (especially with 1 atom or, preferably, more than 1 atom of phosphorus P per metal atom of the catalyst). The term also embraces what is known as incomplete inhibition, if the amount of inhibitor incorporated is insufficient. In this latter case in particular, inhibition may be completed by separate incorporation of the same kind of inhibitor or by way of another inhibitor.

According to one preferred embodiment the composition comprises as solvent an organosilicon compound, such as a silane, a siloxane, a silicone oil and/or a silicone gum. The composition may therefore comprise one or more unsaturated silanes and/or one or more unsaturated siloxanes containing one or more siloxane units (e.g. from 2 to 200, preferably from 2 to 30). The compounds in question are preferably vinylsilanes and/or vinylsiloxanes. Further details regarding their nature will be given later on. The silanes and siloxanes described in U.S. Pat. No. 3,775,452 and U.S. Pat. No. 3,715,334, which are referred to later on, are possible versions. The composition may further comprise one or more silicone oils or gums such as those which are described later on, and which embrace alkenyl types, especially vinyl types, and other types (e.g. based on units of the formula (V), which is defined later on).

According to one particular version the invention relates to a catalyst composition or assembly comprising, optionally in an organosilicon solvent as described above, the metal catalyst capable of catalysing a hydrosilylation reaction and an inhibitor of formula (I) in which:

R, $R^1$, $R^2$, $R^3$ and $R^4$, which are identical or different, represent a linear, branched or cyclic alkyl radical or an aryl radical which is substituted or unsubstituted, especially:
  a linear or branched alkyl radical having 2 to 30 carbon (C) atoms, preferably 2 to 12 C, an alkyl radical containing one or more rings, especially 1 or 2, it being possible in particular for one ring to have 4 to 14 C, preferably 5 to 8 C, or an aryl or alkylaryl radical containing one or more fused or unfused aromatic rings, especially 1 or 2 rings, it being possible for one ring to contain 4 to 14 C, preferably 6 to 8 C, which is or are optionally substituted by 1 or more, especially 1 to 2, linear or branched alkyl(s), especially having 1 to 12 C, preferably 4 to 12 C.

The text below applies to the various embodiments and versions defined above. In the formula (I), R is advantageously a cyclic alkyl radical and more preferably an aryl radical, especially biphenyl.

$R^1$, $R^2$, $R^3$ and $R^4$ are advantageously cyclic alkyl radicals and more preferably aryl radicals, and more preferably still alkylaryl radicals, especially substituted phenyl, e.g. tert-butylphenyl. $R^1$, $R^2$, $R^3$ and $R^4$ are preferably identical.

As inhibitor, preference is given to compounds containing cyclic alkyl or aryl radicals, owing to their inhibitory activity lasting longer than that of the compounds containing linear or branched alkyl radicals.

Preferred inhibitors are of the formula (II):

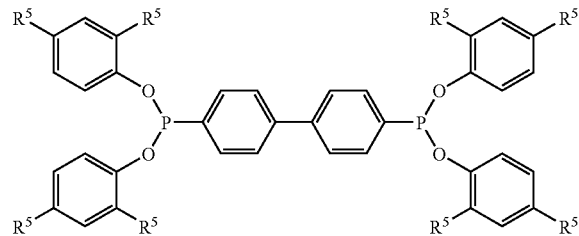

in which the radicals $R^5$, which are identical or different, preferably identical, are linear or branched alkyls having in particular 1 to 12 C, preferably 4 to 12 C.

The preferred inhibitor is of the formula (III):

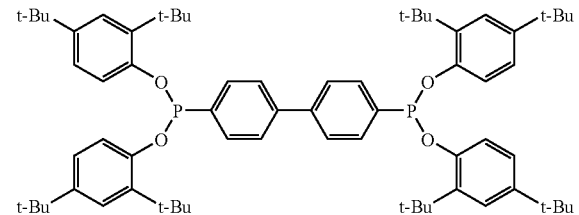

CAS No.: 38613-77-3.

The molar ratios of catalyst metal to inhibitor may be between 1/0.5 and 1/10, preferably between 1/1 and 1/5.

The catalysts to which the invention relates include all catalysts useful for hydrosilylating POS which bear Si—H units and POS which bear Si-[ethylenic or acetylenic unsaturation] units. The compounds in question may therefore be compounds of platinum, of rhodium, or iridium, of nickel, of ruthenium and/or of palladium. More particularly they are compounds of iridium or, more preferably, of platinum.

The compound of platinum may be any complex of platinum and an organic product, examples being those described in U.S. Pat. No. 3,159,601, U.S. Pat. No. 3,159,602, U.S. Pat. No. 3,220,972 and European patents EP-A-0 057 459, EP-A-0 188 978 and EP-A-0 190 530, or any complex of platinum and vinyl organo-siloxanes, examples being those described in U.S. Pat. No. 3,419,593, U.S. Pat. No. 3,715,334, U.S. Pat. No. 3,377,432 and U.S. Pat. No. 3,814,730.

Mention may be made of chloroplatinic acid, an alcohol-modified chloroplatinic acid or else a complex of chloroplatinic acid with an olefin, an aldehyde or a vinylsiloxane, among others. U.S. Pat. No. 2,823,218 discloses a chloroplatinic acid hydrosilylation catalyst and U.S. Pat. No. 3,419,593 relates to catalysts formed by complexes of chloroplatinic acid and vinylsiloxane-type organosilicone. Complexes of platinum and hydrocarbons which are useful as a hydrosilylation catalyst are disclosed by U.S. Pat. Nos. 3,159,601 and 3,159,602. U.S. Pat. No. 3,723,497 describes a platinum acetylacetonate and U.S. Pat. No. 3,220,972 provides catalysts based on platinum alkoxide.

The invention relates more particularly to platinum/unsaturated siloxane complexes, particularly platinum/vinylsiloxane complexes, especially those obtained by reacting a platinum halide with an unsaturated organosilicon material such as an unsaturated silane or an unsaturated siloxane, in accordance for example with the teaching of U.S. Pat. No. 3,775,452 and U.S. Pat. No. 3,715,334, to which the skilled person may refer. The invention applies preferably to Karstedt solutions or Karstedt complexes.

The catalyst assembly according to the invention comprises a mixture of the catalyst and the inhibitor that leads to a new type of complex species between these two compounds. Without wishing to be bound to any specific theory, it is thought that, starting from the Karstedt complex and an inhibitor of formula (I), the new species (I') exhibits a structure of the following type:

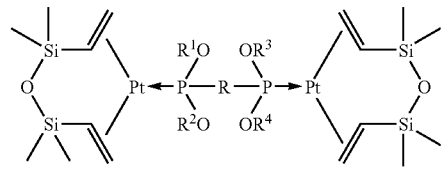

where R, $R^1$, $R^2$, $R^3$ and $R^4$ have the same meanings as for formula (I).

With the inhibitors of formula (II) and (III), without wishing to be bound to any specific theory, it is thought that the new species (II') and (III') have, respectively, the following structures:

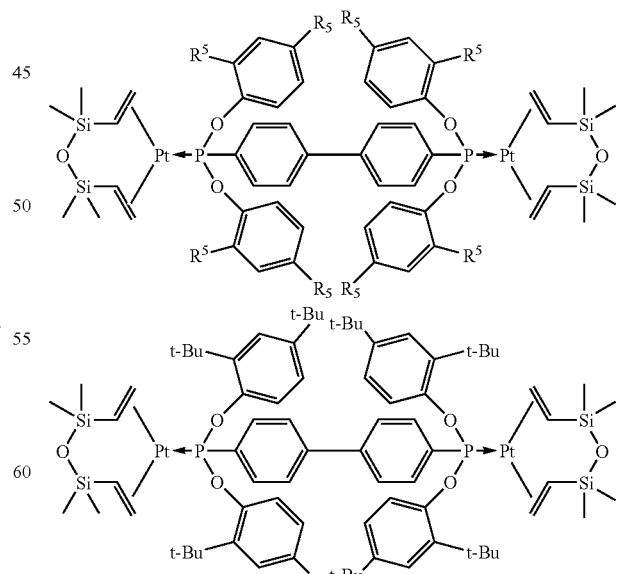

In formulae (I'), (II') and (III') the arrows represent the interactions between the orbitals of the P and Pt atoms.

The present invention also provides:
these new species,
the use of a compound of formula (I), especially (II) and preferably (III), as an inhibitor of a metal catalyst, especially a platinum catalyst, in particular a hydrosilylation catalyst, especially in a one-component silicone composition which crosslinks by way of hydrosilylation reaction, and
the use of mixtures of catalyst and inhibitor according to the invention, and of these new species, as a catalyst in compositions catalysed in particular by platinum, especially silicone compositions which crosslink by way of hydrosilylation reactions, and more particularly still the one-component compositions according to the invention.

As explained elsewhere, the catalyst is inhibited by the inhibitor at room temperature. Its activation may be brought about by temperature increase.

Very advantageously the inhibitors according to the invention, such as the inhibitors of formula (II) and (III), are soluble in unsaturated silanes, especially vinyl silanes such as vinyltrimethoxysilane (VTMO), and in unsaturated siloxanes, examples being vinylsiloxanes, and in platinum/unsaturated silane and platinum/unsaturated siloxane solutions, e.g. platinum/vinylsiloxane solutions. This results in a greater ease of use in the case of mixing with silicone oils. For preparing a catalyst solution of this kind, the solution of catalyst and the inhibitor can be mixed until the inhibitor dissolves completely. Preferably the inhibitor is added to the catalyst solution.

In order to endow the one-component silicone compositions with the best possible properties in terms of inhibition of the hydrosilylation reaction and of controlled pot life, the applicant has developed a specific production procedure. A catalyst assembly or additive (or catalyst composition) in which catalyst and inhibitor are present in complex form is prepared to start with. The catalyst is therefore inhibited at room temperature. This additive is intended for addition to the one-component silicone composition under conditions which ensure fine and homogeneous dispersion.

The present invention therefore likewise provides a process for preparing a catalyst assembly or additive (or catalyst composition) comprising an inhibitor/catalyst pairing. This process applies to the inhibitors of formula (I) and their described variants, and also to other effective organophosphorus compounds, and especially to the inhibitors of general formula (VIII) P(OR)$_3$, in which R is an alkylaryl radical having in particular 7 to 31 carbon atoms, preferably substituted phenyl radicals, substituted for example by linear or branched alkyls, preferably identical, having in particular 1 to 12 C, preferably 4 to 12 C, for example t-Bu.

Among the compounds of formula (VIII), those of the formula (IX) below are preferred:

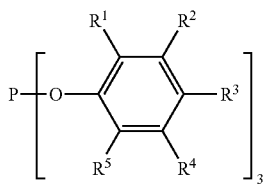

in which R$^1$, R$^2$, R$^3$, R$^4$ and R$^5$, which are identical or different, represent H, a linear or branched aliphatic radical which is saturated, of formula C$_n$H$_{2n+1}$, or unsaturated, of formula C$_m$H$_{2m-1}$, or a radical of formula C$_n$F$_{2n+1}$, with n=1 to 15, and m=3 to 15, it not being possible for all of these radicals together to represent H. Preferably, R$^2$, R$^4$ and R$^5$ represent H and R$^1$ and R$^3$ represent aliphatic radicals, preferably identical aliphatic radicals, e.g. t-Bu.

It is possible to calculate the amounts to be employed in terms of the ratio of catalyst metal to inhibitor. For inhibitors of type (I) this ratio may be between 1/0.5 and 1/10, preferably between 1/1 and 1/5. For inhibitors of type (VIII) this ratio may be between 1/1 and 1/10, preferably between 1/2 and 1/5.

According to one particular version at least one inhibitor of formula (I) and at least one inhibitor of formula (VIII) are used (for example, an inhibitor of formula (II), especially (III), and an inhibitor of formula (IX)). The amounts of inhibitors may be determined so as to maintain substantially the ratio P of inhibitor/catalyst Pt resulting from the application of the ratios set out above. For example, the respective amounts of the inhibitors are selected so as to ensure a ratio of catalyst metal to phosphorus of between 1/1 and 1/10.

In a first embodiment of the process of the invention (embodiment 1 below) a solution comprising the catalyst and the inhibitor is prepared by mixing the organophosphorus inhibitor into the catalyst in solution in an unsaturated silane, e.g. vinylsilane, or an unsaturated siloxane, preferably unsaturated siloxane such as vinylsiloxane, e.g. in the platinum/unsaturated siloxane solution, in particular in the platinum/vinylsiloxane solution, preferably in the Karstedt solution. U.S. Pat. No. 3,775,452, to which the skilled person may refer, describes unsaturated silanes and unsaturated siloxanes under the formulae (1) and, respectively, (2) to (5). U.S. Pat. No. 3,715,334, to which the skilled person may refer, describes vinylsilanes and vinylsiloxanes under the formulae (1) and, respectively, (2) to (5). The content of these US patents, and especially the description of their formulae (1) to (5) describing silanes and siloxanes highly suitable for the invention, is incorporated here by reference.

As has been seen above, the inhibitors of formula (I), especially the inhibitors of formula (II) and (III), are soluble in unsaturated silanes and siloxanes, thereby allowing these inhibitors to be dissolved quickly and easily in a catalyst solution, especially a siloxane-type catalyst solution, e.g. in Karstedt solution, and allowing rapid and effective inhibition of the catalyst.

In the case of the inhibitors of formula (VIII), for example (IX), which are not soluble, the inhibitor is merely dispersed in the catalyst solution. The inhibition of the catalyst takes a little bit longer to obtain.

Generally speaking the catalyst/inhibitor solution may contain from 0.1% to 15%, preferably from 5% to 10%, by weight of platinum metal. Mixing may be carried out by any conventional stirring means, e.g., with a blade mixer.

Complexation, which is the formation in situ of the inhibitor/catalyst complex, is very rapid, particularly of the order of a few minutes.

In a second embodiment (embodiment 2 below) the process comprises
  dispersing the organophosphorus inhibitor in a silicone gum and/or oil,
  heating the silicone gum or oil to a temperature greater than the melting or softening temperature of the inhibitor,
  adding and mixing the catalyst.

The silicone gum or oil is heated to the appropriate temperature before, during and/or after the addition of the organophosphorus derivative. According to one preferred version the organophosphorus compound is first dispersed in the oil or gum, which is held at a temperature below the melting point, and then the composition is heated to a temperature greater than the melting or softening temperature of the organophosphorus compound.

The organophosphorus compound undergoes rapid, effective and homogeneous dispersion in the silicone gum or oil. It is possible in general to consider a dispersion time of more than a few minutes, in particular of the order of 5 minutes to 1 hour, preferably 15 minutes to 30 minutes, to be sufficient.

The silicone material is preferably heated to a temperature greater by 1 to 50° C., in particular from 5 to 20° C., more preferably 10 to 20° C., above the melting or softening temperature of the organophosphorus compound used. At the selected temperature the mixture of silicone material and inhibitor is kept stirring for a time sufficient to ensure effective melting of the dispersed organophosphorus compound. It is possible in general to consider a heating and stirring time of more than a few minutes, in particular of the order of 5 minutes to 1 h, preferably 15 minutes to 30 minutes, to be sufficient.

The catalyst may then be added to the composition obtained beforehand. In order to prevent the catalyst being denatured, if necessary, the composition from before is cooled to a temperature less than the denaturation point of the catalyst. Generally speaking it is preferred to take the above composition to ambient temperature, e.g. of the order of 25° C.

According to one preferred version of this preparation embodiment, after the above composition has cooled, especially to room temperature, the Karstedt solution or complex is added and the mixture is stirred.

Mixing is continued until the catalyst is homogeneously dispersed in the silicone material and an inhibitor/catalyst complex, generated in situ is formed, which notably is dispersed finely and homogeneously in the silicone oil or gum.

The silicone oil or gum, or a mixture, used to form this solution is selected so as to be compatible with the end silicone composition. According to one preferred version an oil, gum or mixture is used whose viscosity is close to or the same as that of the end silicone composition or of the portion of the latter in which the inhibitor/catalyst solution will first be mixed. In particular it is possible to use an oil or gum which is identical or nearly identical to one or more compounds of the end silicone composition. Thus it is possible to use an oil or a gum containing an alkenyl group (alkenylated), preferably a vinyl group, such as the POS A according to the invention, and more preferably still the POS A forming part of the one-component silicone composition referred to. It is also possible to use a polyorganosiloxane gum or oil C formed from siloxyl units, of the formula (V) defined later on. The oil or gum in question may in particular be a polydimethylsiloxane (PDMS) oil or gum. The viscosity of these non-vinyl (non-alkenyl) oils or gums may range from a few mPa/s to several millions of mPa/s, it being possible for the selection to depend in particular on the type of end silicone composition, e.g. RTV, LSR or HTV elastomer, to which the text below relates. The mixing of the ingredients at the various stages is carried out by means of a mixing device adapted to the viscosity of the oil or gum used. For relatively high viscosities, as in the case of the oils or gums used in HTV elastomers, it is possible to employ a roll mill or an arm-type mixer.

In the two embodiments 1 and 2 it may be useful to add to the composition that is obtained each time one or more ingredients intended to facilitate mixing with the end silicone composition. The facilitation in question may in particular involve adapting the viscosity, in order to bring it closer to that of the constituent or mixture of constituents of the end silicone material to which the additive is added. The ingredient in question may in particular be a silicone gum or oil having a viscosity which is compatible with the POS A. Depending on the silicone composition, the skilled person is perfectly capable of selecting an appropriate oil or gum, appropriate particularly in terms of viscosity, to dilute the inhibitor/catalyst composition obtained beforehand. According to one particular version an oil or gum is employed which is selected in particular from the above-defined oils or gums C, especially PDMS, or else from the POS A described with reference to the silicone composition.

The additive obtained in accordance with embodiment 1 or embodiment 2, after possible dilution in an oil or gum, contains preferably from 0.001% to 10%, more preferably from 0.01% to 1%, by weight of platinum metal.

Preferably the additive thus obtained (embodiment 1 or 2) is a simple paste intended for subsequent addition to the silicone composition proper. In other words, this additive constitutes a fraction of the final one-component silicone composition. According to one advantageous embodiment the paste is based on one of the constituents of this composition and in particular is based on the POS A or based on PDMS.

The catalyst compositions or additives or assemblies obtained by employing the preparation embodiments described above are likewise provided by the present invention. They preferably comprise at least one inhibitor of formula (I), (II), (III), (VIII) or (IX) and a catalyst in accordance with the invention.

According to one first embodiment the catalyst composition comprises the catalyst, the inhibitor and an unsaturated silane, or an unsaturated siloxane, containing one or more siloxane units (e.g. from 2 to 200, preferably from 2 to 30), in particular in accordance with the teaching of U.S. Pat. No. 3,775,452 and U.S. Pat. No. 3,715,334 referred to above. The compounds in question are preferably vinylsilanes and/or vinylsiloxanes. According to one particular arrangement the composition is obtained from a platinum/unsaturated silane or platinum/unsaturated siloxane solution, in particular a platinum/vinylsiloxane solution, obtained especially by reacting a platinum halide and an unsaturated organosilicon material such as an unsaturated silane or an unsaturated siloxane, an example being the Karstedt solution or complex.

According to a second embodiment the catalyst composition comprises the catalyst, the inhibitor, a silicone oil or gum, and optionally a silane or a siloxane as described above. The oil or gum is preferably identical or similar to one or more compounds of the end silicone composition. It is preferred to use an oil or a gum containing an alkenyl group, preferably a vinyl oil or gum, such as the POS A according to the invention, and more preferably still the POS A forming part of the intended one-component silicone composition. It is also possible to have a polyorganosiloxane gum or oil C, e.g. a PDMS.

According to one first version the catalyst composition comprises at least one inhibitor of formula (I), (II) or (III), optionally in combination with an inhibitor of formula (VIII) or (IX), and an oil or gum containing an alkenyl group, preferably a vinyl oil or gum, preferably POS A, and/or a polyorganosiloxane oil or gum C, preferably PDMS.

According to a second version the catalyst composition comprises or is essentially composed of at least one inhibitor of formula (VIII) or (IX) and a polyorganosiloxane gum or oil C, preferably PDMS.

In the catalyst composition the inhibitor inhibits the catalytic action of the catalyst at room temperature. In particular, inhibitor and catalyst are in complexed form.

The invention particularly provides an additive of this kind in which the assembly of catalyst+inhibitor represents from 0.001 to 40% by weight, preferably from 0.01 to 30%, more preferably from 0.1 to 20%.

The present invention additionally provides a silicone composition which is crosslinkable by hydrosilylation and comprises at least one PolyorganoSiloxane (POS) A bearing ethylenic and/or acetylenic unsaturation(s), at least one hydrogenated polyorganosiloxane B (POS B below) and also (a) a hydrosilylation catalyst and an inhibitor of formula (I), (II) or (III), or (b) a catalyst assembly obtained as described above.

By definition, throughout the present description, when it is said that a silicone composition or a catalyst additive or assembly comprises such or such an inhibitor of formula (I), (II), (III), (VIII) or (IX), the reference should be understood as being to the free inhibitor, to the inhibitor complexed to the catalyst, or to a mixture of these two species.

According to the preferred version of the invention the composition comprises a catalyst additive or assembly according to the invention, preferably brought into the form of a paste prepared in accordance with one of the above-defined preparation embodiments 1 and 2.

In a less preferred variant, the catalyst and the inhibitor are added separately to the silicone composition. In that case it is preferable to add them to POS A or to a composition containing POS A and one or more other ingredients, with the exception of POS B. POS B is incorporated after thorough mixing of the POS A, the catalyst and the inhibitor, and advantageously after a certain latency time. For its incorporation the inhibitor may advantageously be in solution in a vinylsiloxane.

The invention relates both to polyaddition silicone compositions which are room-temperature-vulcanizable (RTV; their crosslinking may be accelerated at high temperature) and to high-temperature-vulcanizable (HTV) elastomers. They are well known to the skilled person, who may refer, for example, to U.S. Pat. No. 3,220,972, U.S. Pat. No. 3,284,406, U.S. Pat. No. 3,346,366, U.S. Pat. No. 3,697,473 and U.S. Pat. No. 4,340,730.

As is known per se, POS A may be formed in particular of siloxyl units of formula:

$$Y_a Z_b SiO_{\frac{(4-a-b)}{2}} \quad (IV)$$

in which Y is a $C_2$-$C_6$ alkenyl, preferably vinyl, Z is a monovalent hydrocarbon group which does not have any adverse effect on the activity of the catalyst, Z being selected generally from alkyl groups having 1 to 8 carbon atoms inclusive, such as methyl, ethyl, propyl and 3,3,3-trifluoropropyl groups, and aryl groups, such as xylyl, tolyl and phenyl, a is 1 or 2, b is 0, 1 or 2 and a+b is between 1 and 3, optionally all of the other units being units of average formula:

$$Z_c SiO_{\frac{4-c}{2}} \quad (V)$$

in which Z has the same meaning as above and c has a value of between 0 and 3.

As is known per se, POS B may be formed in particular of siloxyl units of formula:

$$H_d W_e SiO_{\frac{4-d-e}{2}} \quad (VI)$$

in which W is a monovalent hydrocarbon group having no adverse effect on the activity of the catalyst and meeting the same definition as Z, d is 1 or 2, e is 0, 1 or 2, d+e has a value of between 1 and 3, optionally all of the other units being units of average formula:

$$W_g SiO_{\frac{4-g}{2}} \quad (VII)$$

in which W has the same meaning as above and g has a value of between 0 and 3.

These POS A & B are for example, respectively, a polyorganovinylsiloxane and a polyorganohydrosiloxane. The organic substituents other than the reactive groups, vinyl and hydrogen, are for example methyls or cyclohexyls. The hydrogens and vinyls are borne by siloxyl units M=[$R_3$SiO—] and/or D=[—(R)$_2$SiO—] and/or T=[—(R)SiO—]. These hydrogen or vinyl units M or D each contain, respectively, one or more Hs or vinyls, preferably just one.

The number of SiH or SiVi units per molecule is preferably greater than or equal to 2. This may in particular represent from 0.01% to 10% (preferably 0.1 to 2%) of vinyl by weight for POS A and from 0.001% to 5% (preferably 0.05 to 2%) of hydrogen by weight for POS B.

Appropriate POS B are polymethylhydrosiloxanes having —Si($CH_3$)$_3$ end groups and polydimethylsiloxanes having —Si($CH_3$)$_2$H end groups, methylhydro-dimethylsiloxane copolymers having —Si($CH_3$)$_2$H end groups, methylhydromethyl-octylsiloxane copolymers and methylhydrocyclosiloxane polymers.

Generally speaking the POS A & B have an average molecular mass of between $1\times10^2$ and $1\times10^7$ (g/mol).

For POS A, this embraces in particular, in terms of dynamic viscosity at 25° C.:
- in the case of silicone compositions which are high-temperature-vulcanizable (HTV) by polyaddition, POS A having in particular a viscosity of at least $5\times10^5$ mPa·s, preferably between $1\times10^6$ and $1\times10^7$ mPa·s, and even more,
- in the case of silicone compositions which are high-temperature-vulcanizable by polyaddition and are of liquid silicone elastomer (LSR) type, POS A having in particular a viscosity of preferably between $1\times10^4$ and $5\times10^5$ mPa·s, and
- in the case of silicone compositions which are room-temperature-vulcanizable (the vulcanization being accelerated at high temperature) by polyaddition, or RTV compositions, POS A having in particular a viscosity of between 100 and $10^4$ mPa·s, preferably between 1000 and 5000 mPa·s.

The POS B generally have a viscosity of between 10 and 10 000 mPa·s, preferably between 50 and 1000 mPa·s.

According to one preferred version of the invention the silicone compositions concerned are POS which are high-temperature-vulcanizable (HTV) by polyaddition and in which the POS A may have in practice a viscosity at 25° C. of, for example, $1\times10^6$ to $5\times10^6$ mPa·s and the POS B a viscosity at 25° C. of 10 to 5000 mPa·s, in particular from 50 to 1000 mPa·s (e.g. 300 mPa·s).

The viscosity is measured using a BROOKFIELD viscometer as indicated in the standard AFNOR NFT 76 106 of May 1982.

All of the viscosities referred to in the present specification correspond to a magnitude of dynamic viscosity at 25° C. which is referred to as "Newtonian"; that is, the dynamic viscosity which is measured, in a manner known per se, at a shear rate sufficiently low for the measured viscosity to be independent of the shear rate.

According to one particular version of the invention the silicone composition comprising the POS A and B and the catalyst assembly according to the invention may be admixed with an inhibitor of formula (I), (II) or (III), especially in solution in a vinylsiloxane, and/or with another crosslinking inhibitor, of formula (VIII) or (IX) for example, with an acetylenic alcohol (FR-A-2 372 874, FR-A-1 528 464), with a maleate compound (U.S. Pat. No. 4,256,870 and U.S. Pat. No. 4,530,989) or with an acetylene dicarboxylate compound (U.S. Pat. No. 4,504,645 and U.S. Pat. No. 4,347,346).

The silicone compositions of the invention may further comprise customary functional additives. Classes of customary functional additives may include:
  fillers,
  hydroxylated POS oils which are useful as compatibilizers,
  adhesion promoters,
  adhesion modifiers,
  thermal stability additives,
  additives for increasing the consistency,
  pigments,
  thermal stability additives, oil resistance additives, flame retardant additives (for example metal oxides).

The fillers optionally provided are preferably minerals. They may in particular be siliceous.

Siliceous materials may act as a reinforcing or semi-reinforcing filler.

Reinforcing siliceous fillers are selected from colloidal silicas, pyrogenic silica powders and precipitated silica powders, or mixtures thereof. These powders have an average particle size of generally less than 0.1 μm and a BET specific surface area of more than 50 m$^2$/g, preferably between 150 and 350 m$^2$/g.

Semi-reinforcing siliceous fillers, such as diatomaceous earths or ground quartz, may also be employed.

Nonsiliceous mineral materials may play a part as a semi-reinforcing or bulking mineral filler. Examples of these nonsiliceous fillers, which can be used alone or in a mixture, are carbon black, titanium dioxide, aluminum oxide, hydrated alumina, expanded vermiculite, unexpanded vermiculite, calcium carbonate, zinc oxide, mica, talc, iron oxide, barium sulphate and slaked lime. These fillers have a particle size of generally between 0.001 and 300 μm and a BET surface area of less than 100 m$^2$/g.

From a practical but non-limitative standpoint, the fillers employed may be a mixture of quartz and silica.

The fillers may be treated with any appropriate product.

From a weight standpoint it is preferred to employ an amount of filler of between 10% and 50% by weight, preferably between 20% and 40% by weight, relative to the entirety of the constituents of the composition.

More generally, from a quantitative standpoint, the compositions according to the invention are in accordance with standard proportions in the technical field under consideration, bearing in mind that the intended application must also be taken into account.

The invention further provides a process for preparing a hydrosilylation-crosslinkable one-component silicone composition comprising at least one polyorganosiloxane (POS) A bearing ethylenic and/or acetylenic unsaturation(s), at least one hydrogenated polyorganosiloxane B (POS B below), at least one hydrosilylation catalyst and at least one inhibitor of formula (I), (II), (III), (VIII) and/or (IX), in which process the inhibitor and the catalyst are brought into the form of a catalyst additive or assembly prepared beforehand according to the invention, preferably a paste formed from the premixing of the inhibitor and the catalyst. In other words the catalyst is introduced in its inhibited form in combination with the inhibitor. In accordance with what was described above, the inhibition may relate to all or part of the catalyst molecules, depending on the amount of inhibitor present in the additive. The inhibition is preferably complete.

This additive may be brought into the rest of the silicone composition or into any fraction thereof, especially into a fraction comprising or consisting of POS A, POS B or a mixture of POS A and B. The process may also be defined as incorporating the production of the additive as described above and then the bringing of this additive into the silicone composition.

According to one first embodiment of the invention an additive prepared in accordance with embodiment 1 described above (with or without dilution) is added. The additive is therefore obtained from the dispersing of the inhibitor in a solution of the catalyst in an unsaturated silane or siloxane, preferably vinylsiloxane.

According to a second embodiment an additive prepared in accordance with embodiment 2 described above (with or without dilution) is added. In that case the additive is obtained from the mixing of the inhibitor in a silicone gum or oil at a temperature greater than the melting temperature or softening temperature of the inhibitor, followed by addition of the catalyst.

The additive may be added before, during or after addition of other ingredients, such as mineral filler, crosslinking inhibitor, hydroxylated POS oil, or other, customary functional additives such as those described above.

The catalyst additives or assemblies according to the invention may be easily mixed into this silicone composition. The various mixing means commonly employed in the silicone industry may be used, and especially arm-type mixers and roll mills when required by the viscosity, particularly in the case of HTV elastomers. The mixing operation is continued to give optimum dispersion of the catalyst additive or assembly. The skilled worker is capable of determining the optimum conditions.

The invention additionally provides one-component silicone compositions obtainable by employing the preparation process described above, these compositions being characterized in particular by remarkably fine and homogeneous dispersion of the catalyst/inhibitor pairing.

Further provided by the invention is a process for hydrosilylating one or more POS A using one or more POS B, characterized in that it consists in employing a silicone composition as defined above and in heating it to the crosslinking temperature, generally between 50 and 200° C., more particularly between 100 and 150° C. Depending on the composition, the skilled person has no difficulty at all in determining the optimum temperature for initiating the hydrosilylation.

The relative amount of unsaturated compound and of compound containing Si—H unit may be controlled so as to ensure that all of the unsaturations react with Si—H bonds.

In general the molar ratio of the unsaturations to the Si—H bonds varies between 1:10 and 10:1.

According to the invention the hydrosilylation reaction is conducted in the presence of a catalytic amount of the catalyst according to the invention. By catalytic amount is meant less than one molar equivalent of platinum relative to the amount of unsaturations present in the reaction mixture.

Generally speaking it is enough to introduce less than 1000 ppm, preferably less than 100 ppm, more preferably less than 50 ppm of platinum into the reaction mixture, calculated relative to the total mass of the unsaturated compound and of the compound containing Si—H units.

The POS A & B, the catalyst, the compounds of formula (I), (II), (III), (VIII) and (IX) and also the other, conventional additives, such as the fillers, are very readily available products accessible to the skilled person.

The compounds of formula (I), (II) or (III) may be obtained conventionally by reacting (i) a dihalogen compound X—R—X (X being a halogen atom), R being as defined above with respect to formulae (I), (II) and (III), with (ii) an excess of $PCl_3$, then by reacting the compound obtained in the preceding stage with 4 molecules of alcohol R'OH, thereby making it possible to form the groups $R^1$ to $R^4$ of formulae (I), (II) and (III). The resulting product may then be purified using the conventional techniques known to the skilled person. They may also be prepared in accordance with the teaching of U.S. Pat. No. 5,109,043.

The invention will now be described with the aid of non-limitative examples.

EXAMPLES

Example 1

Preparation of a Catalyst Solution Having an Inhibitor (III)/Pt Ratio=0.75 (i.e. P/Pt=1.5)

10 g of a Karstedt platinum solution containing 12.6% of Pt by weight (6.46 mmol of platinum) are placed in a flask equipped with a magnetic stirrer.

5.01 g (4.85 mmol or 0.75 equivalent) of inhibitor (III) according to the invention are added to the above solution with stirring.

Following the addition the reaction mixture is kept with stirring for a few minutes. A catalyst solution is obtained which contains 8.4% of platinum by weight. This clear, homogeneous, readily manipulable solution is used in the following examples.

NMR analysis of this reaction mixture shows the complete disappearance of the Karstedt catalyst.

Example 2

Preparation of a Catalyst Assembly Having an Inhibitor (IV)/Pt Ratio=1.5 (i.e. P/Pt=1.5)

10 g of a Karstedt platinum solution containing 12.6% of Pt by weight (6.46 mmol of platinum) are placed in a flask equipped with a magnetic stirrer. 6.27 g (9.69 mmol or 1.5 equivalent) of an inhibitor according to U.S. Pat. No. 6,300,455 are added to the above solution with stirring. This inhibitor, of formula (IX) above, conforms more specifically to the formula (X) below:

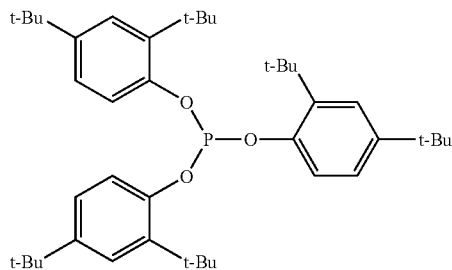

Following the addition the reaction mixture is heterogeneous. It remains heterogeneous even after several minutes of stirring. After 3 h of stirring the reaction mixture becomes heterogeneous and white in colour. Stopping the stirring causes the white solid to decant to the bottom of the flask.

NMR analysis of this reaction mixture shows the complete disappearance of the Karstedt catalyst.

Example 3

Composition According to the Invention (All Parts are Given by Weight)

A/Preparation

In a Z-arm mill an HTV base 1 is prepared by mixing the following for 2 hours at room temperature (23° C.):

100 parts of a vinyl-containing polydimethylorganosiloxane containing 720 ppm of groups Vi in the chain and having a viscosity of 5 million mPa·s at 25° C., 33 parts of surface-treated pyrogenic silica with a specific surface area of 60 m²/g, 13 parts of an untreated silica with a specific surface area of 150 m²/g and 6 parts of a compatibilizing agent, which is a hydroxyl-containing polyorganosiloxane oil.

The following components are added to this preparation on rolls:

0.604 part of a polydimethylorganosiloxane oil containing 30% by weight of —SiH groups and having a viscosity of 30 mPa·s at 25° C.

2.5 ppm of platinum metal, brought into the form of the catalyst assembly of Example 1.

6.25 ppm of inhibitor (III) in solution in a vinylsiloxane.

B/Characterization of the composition:

One fraction of the homogeneous mass obtained is used for measuring the rheometric properties of the silicone elastomer in the course of vulcanization of the polyorganosiloxane composition at 140° C.

This characterization is conducted in accordance with standards NF T43015 and ISO 6502. A specimen of catalysed elastomer is compressed in an airtight chamber under a given pressure and at a given temperature. The chamber is formed from two half-chambers, one of which is subjected to linear or rotational (disc) oscillations of low amplitude. This action produces in the specimen an alternative sinusoidal deformation, linear or in torsion, and a sinusoidal shearing torque or force which depend on the stiffness (shear modulus) of the elastomer. The stiffness of the specimen increases in line with the vulcanization or polyaddition reaction. Measuring the torque required for the oscillation of the disc over time makes it possible to obtain, at the end of measurement, the vulcanization characteristics of the elastomer.

Rheometric properties recorded at 140° C.:

ts2: scorch time (Cmin+2 points), corresponding to the vulcanization time t50: time required to obtain 50% of the value of Cmax t90 time required to obtain 90% of the value of Cmax Cmin: minimum elastic torque applied (also called S'mini)

Cmax: maximum elastic torque applied (also called S'maxi)

Vmax: maximum vulcanization rate attained.

| Characteristics | Values |
|---|---|
| ts2 | 20 s |
| t50 | 47 s |
| t90 | 389 s |
| Cmin | 1 dNm |
| Cmax | 10.7 dNm |
| Vmax | 12.6 dNm/min |

Pot Life

After 4 weeks of ageing at room temperature the mixture has still not crosslinked.

The entirety of these results shows that the novel catalyst assembly claimed is characterized by great ease of use and by high-performance catalyst properties (as measured by rheometry).

Example 4

Preparation In Situ, by a High-Temperature Process, of an Additive Based on a Silicone Matrix, Karstedt Platinum and Inhibitor (III)

4a/In an arm-type mixer, 0.261 g of inhibitor (III) is added to 100 g of an HTV base 2 with a hardness of 35. After mixing for 10 minutes, the temperature of the reaction mixture is raised to at least 100° C., a temperature higher than the softening temperature—75-95° C.—of inhibitor (III). After mixing for 10 minutes, the reaction mixture is allowed to cool to 25° C. Observation of the mixture does not reveal the presence of agglomerates in the elastomer matrix.

4b/Subsequently, either on a roll mill or in an arm-type mixer, 0.375 g of Karstedt catalyst is added (platinum in oxidation state zero in solution in a vinylsilicone oil) (10% by mass of platinum).

Note: for all of Examples 4 to 10 an HTV base 2 was used which was composed of:

- 50 parts of vinyl-containing polydimethylorganosiloxane containing 720 ppm of vinyl groups in the chain and having a viscosity of 5 million mPa·s at 25° C.,
- 50 parts of vinyl-containing polydimethylorganosiloxane containing 120 ppm of vinyl groups in the chain and having a viscosity of 5 million mPa·s at 25° C.,
- 30 parts of surface-treated pyrogenic silica with a specific surface area of 55 m$^2$/g, and
- 1.22 parts of a compatibilizing agent, which is a hydroxyl-containing polyorganosiloxane oil.

Comparative Example 5

Preparation on a Roll Mill, by a Cold Process, of an Additive Based on a Silicone Matrix, Karstedt Platinum and Inhibitor (III)

On a roll mill 1.305 g of inhibitor (III) as a powder are added to 500 g of the HTV base 2 with a hardness of 35. Following incorporation, 1.875 g of Karstedt catalyst are added dropwise.

Comparative Example 6

Preparation in an Arm-Type Mixer, by a Cold Process, of an Additive Based on a Silicone Matrix, Karstedt Platinum and Inhibitor (III)

The same type of additive described in Example 5 was produced using an arm-type mixer.

6a/1.048 g of inhibitor as a powder are added to 400 g of the HTV base 2 with a hardness of 35. Mixing is continued for 20 minutes.

6b/1.5 g of Karstedt catalyst are subsequently added to the reaction mixture.

Examples 7 and 8

Evaluation of the Various Additives Prepared According to Examples 4 and 6

The various additives described in Examples 4 and 6 were tested in an HTV formulation for the one-component polyaddition application.

The composition of this HTV formulation is as follows: 100 g of an HTV base 1 according to Example 3 is admixed using a roll mill with 0.94 part of —SiH— containing oil (440 meq —SiH/100 g of oil, viscosity 250 mPa·s). Following incorporation, and then after 15 passes between the two rolls (improving the dispersion of the additives), 0.037 part of an additive composed of the HTV base 2 with a hardness of 35 and of inhibitor (III) according to Examples 4a and 6a is added. Following incorporation, and then 15 passes of the composition between the two rolls, 0.267 part of the additive composed of the HTV base, inhibitor (III) and Karstedt platinum (Examples 4 and 6 above) is added. The amount of platinum is 1 ppm. 15 passes between the two rolls are also carried out. The results in terms of uncured appearance of the formulations produced, kinetic characteristics and changes in the formulation after 3 months at 25° C. are reported in Table 2.

Example 9

Stability of the Additives Prepared According to Example 4

In order to follow the stability of these additives and the kinetics of complexation between the Karstedt platinum, the additives prepared according to Example 4 were evaluated over time. Via an HTV formulation for the one-component polyaddition application, identical to that described in Example 7, the complexation of the platinum by the inhibitor and the stability of this additive were monitored by way of measurements determined by rheometry (Table 3).

Discussion of the Results Obtained with Examples 4 to 9

The additives prepared cold from inhibitor (III) and the Karstedt platinum (Examples 5 and 6) contain agglomerates whose average diameters vary depending on the type of tool employed (Table 1). This means that these additives are not as highly performing as the additive prepared at high temperature according to Example 4 (Table 2). These additized one-component HTV formulations according to Examples 5 and 6, however, remain stable after three months of ageing.

For the additive prepared according to Example 4 no problem caused by the incorporation of the inhibitor and then of the Karstedt platinum is noted. The uncured additive is homogeneous. It exhibits no defects (Table 1). The one-component HTV formulation additized with these additives is stable after 3 months of ageing, and no change is observed in the quality of the mouldings (Table 2). Rheometric monitoring of the complexation between the inhibitor and the Karstedt platinum shows that this complexation is extremely rapid. The values obtained on day 0 are of the same order as those obtained after 18 days. Moreover, the values over this period are homogeneous, indicating the stability of the additive (Table 3).

CONCLUSION

Employing the high-temperature process allows additives to be obtained whose active species are very well dispersed. The high quality of these additives goes hand in hand with the high quality and stability of the final one-component HTV formulations.

TABLE 1

Characteristics, in the uncured state, of the additives produced

| Example | | 4 | 5 | 6 |
|---|---|---|---|---|
| Preparation of the additive | System Employed | Inhibitor (III), Karstedt platinum | | |
| | | Arm-type mixer | Roll mill | Arm-type mixer |
| | Incorporation phase | No problem | No problem | No problem |
| Appearance of the additive after preparation | | Homogeneous | Heterogeneous, agglomerates with a diameter of 0.5 to 0.8 mm | Hererogeneous, agglomerates with a diameter of 0.3 to 0.5 mm |

TABLE 2

Characteristics of the one-component HTV formulations according to the examples

| Example | | 7 | 8 |
|---|---|---|---|
| Additive utilized | | Example 4 | Example 6 |
| Characteristics | | Inhibitor (III), Karstedt platinum Arm-type mixer | Inhibitor (III), Karstedt platinum Arm-type mixer |
| Appearance of the mouldings after curing for 8 min at 140° C. | | No defects, homogeneous | Under-crosslinked areas, presence of gels |
| Rheological characteristics | ts2 | 30 | 30 |
| | t50 | 52 | 55 |
| | t90 | 428 | 438 |
| | Cmin | 1.59 | 1.82 |
| | Cmax | 9.15 | 9.02 |
| | Vmax | 8.2 | 7.1 |
| Changes in the formulation in the uncured state after 3 months | | Effective replastification | Effective replastification |

TABLE 3

Changes in the additive prepared according to Example 4
Evaluation of the corresponding one-component HTV formulations

| | Age of the additive of Example 4 | | | | | |
|---|---|---|---|---|---|---|
| | 0 d | 1 d | 2 d | 5 d | 6 d | 18 d |
| ts 2 (sec.) | 24 | 25 | 24 | 23 | 25 | 26 |
| t50 (sec.) | 53 | 51 | 46 | 46 | 57 | 54 |
| t90 (sec.) | 412 | 426 | 411 | 403 | 439 | 410 |
| Cmin (dNm) | 1.04 | 0.99 | 0.97 | 0.93 | 0.97 | 1.02 |
| Cmax (dNm) | 8.46 | 7.88 | 7.47 | 7.70 | 8.02 | 8.20 |
| Vmax (dNm/Min) | 8.6 | 8.8 | 7.47 | 7.70 | 8.02 | 8.3 |

Example 10

Preparation of Catalyst/inhibitor (III) or (X) Complexes

Catalyst 1:

3.6 g of Karstedt catalyst at a concentration of 12% by weight of platinum in divinyltetramethyldisiloxane (DVTMS) are admixed by spatula and with vigorous magnetic stirring with 1.32 g of compound (III) (so that the P/Pt molar ratio=1.2). After a few minutes a homogeneous and readily manipulable fluid solution (C1) is obtained. It contains 7.65% of platinum by weight and is used directly in the examples which follow.

Catalyst 2:

4.3 g of Karstedt catalyst at a concentration of 10% by weight of platinum in DVTMS is admixed by spatula and with magnetic stirring with 1.7 g of compound (X) (so that the P/Pt molar ratio=1.2). After a few minutes a heterogeneous reaction mixture (C2) is obtained. It contains 7.2% of platinum by weight and is used directly in the examples which follow.

Example 11

Evaluation of the Quality of Inhibition Provided by C1 and C2

A reaction system is prepared by mixing 20 grams of an organovinylpolysiloxane having a viscosity of 230 mPa·s and containing 0.61% of vinyls by weight with the catalyst mixture C1 or C2 so as to give 80 ppm by weight of platinum in the final mixture; subsequently 5.4 grams of an organohydrosiloxane having a viscosity of 300 mPa·s and containing 0.17% by weight of hydrogen are added. This final reaction mixture is homogenized by stirring for 5 minutes.

To assess the quality of the inhibition, the gel time $t_{gel}$, corresponding to the time for the reaction mixture to set, is measured at room temperature. The comparative reactivity of the two systems is evaluated by DSC (Differential Scanning Calorimetry).

| Catalyst mixture | $t_{gel}$ | DSC | | |
|---|---|---|---|---|
| | | $t_{peak}$ (° C.) | $t_{endset} - t_{onset}$ (° C.) | $\Delta H°$ (kJ/mol) |
| C1 | >24 hours | 104 | 12 | 20.7 |
| C2 | >24 hours | 109 | 19 | 20.4 |

Comparative Example 12

A reaction system is prepared by mixing 20 grams of an organovinylpolysiloxane having a viscosity of 230 mPa·s and containing 0.61% of vinyl by weight, the amount of organophosphorus inhibitor (III) or (X) required to give a P/Pt ratio of 1.2, then the Karstedt catalyst (14.3% solution of platinum in DVTMS) so as to give 80 ppm by weight of platinum in the final mixture. This mixture is stirred for 10 minutes at room temperature and then 5.4 grams of an organohydrosiloxane having a viscosity of 300 mPa·s and containing 0.17% by weight of hydrogen are added. This final reaction mixture is homogenized by stirring for a few minutes.

To assess the quality of the inhibition, the gel time, corresponding to the time taken for the reaction mixture to set, is measured at room temperature.

| Inhibitor | $t_{gel}$ |
|---|---|
| (III) | <5 minutes |
| (X) | <5 minutes |

Examples 11 and 12 show that:
- to obtain high-performance inhibition it is preferable to incorporate the platinum in a pre-complexed form rather than to carry out this complexation directly in the final reaction mixture.
- The inhibitor of type (III) gives homogeneous catalyst systems in DVTMS, which greatly facilitates their use.
- The reactivities of the two catalyst systems are comparable.

It should be well understood that the invention defined by the attached claims is not limited to the specific embodiments indicated in the above description but embraces the variants thereof which are not outside either the scope or the spirit of the present invention.

What is claimed is:

1. A process for preparing a hydrosilylation-crosslinkable one-component silicone composition comprising at least one polyorganosiloxane (POS) A bearing ethylenic and/or acetylenic unsaturation(s), at least one polyorganohydrosiloxane (POS) B, a hydrosilylation catalyst and an inhibitor which is an organophosphorus compound inhibiting the action of the catalyst at room temperature, said process comprising premixing said hydrosilylation catalyst and said inhibitor to form a catalyst/inhibitor additive and then combining said additive with said at least one polyorganosiloxane (POS) A bearing ethylenic and/or acetylenic unsaturation(s) and said at least one polyorganohydrosiloxane (POS) B, wherein said inhibitor is of the following formula (I):

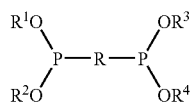

in which:
R, $R^1$, $R^2$, $R^3$ and $R^4$, which are identical or different, represent a linear, branched or cyclic alkyl radical or an aryl or alkylaryl radical which is substituted or unsubstituted;

or wherein the inhibitor is of formula (VIII) $P(OR)_3$ in which R is an alkylaryl radical having 7 to 31 carbon atoms, wherein the premixing to form the catalyst/inhibitor additive is carried out by mixing the inhibitor in a silicone gum or oil at a temperature greater than the melting temperature or softening temperature of the inhibitor, followed by cooling, followed by addition of the catalyst.

2. The process according to claim 1, wherein the inhibitor has formula (I) wherein each linear or branched alkyl radical has 2 to 30 carbon (C) atoms.

3. The process according to claim 2, wherein each linear or branched alkyl radical has 2 to 12 C atoms.

4. The process according to claim 1, wherein the inhibitor has formula (I) wherein each cyclic alkyl radical has one or more rings having 4 to 14 C atoms.

5. The process according to claim 4, wherein each cyclic alkyl radical has 1 or 2 rings having 5 to 8 C atoms.

6. The process according to claim 1, wherein each aryl or alkylaryl radical has one or more fused or unfused aromatic rings having 4 to 14 C atoms, which is or are optionally substituted by 1 or more linear or branched alkyl(s) having 1 to 12 C atoms.

7. The process according to claim 6, wherein each aryl or aralkyl radical has 1 or 2 fused or unfused aromatic rings having 6 to 8 C atoms which is or are optionally substituted by 1 or more linear or branched alkyl(s) having 1 to 12 C atoms.

8. The process according to claim 7, wherein each aryl radical is a substituted phenyl radical.

9. The process according to claim 1, wherein in the formula (I), R is a cyclic alkyl radical or an aryl radical.

10. The process according to claim 9, wherein R is biphenyl.

11. The process according to claim 1, wherein in the formula (I), $R^1$, $R^2$, $R^3$ and $R^4$ are cyclic alkyl radicals, aryl radicals or alkylaryl radicals.

12. The process according to claim 11, wherein $R^1$, $R^2$, $R^3$ and $R^4$ are substituted phenyl radicals.

13. The process according to claim 1, wherein the inhibitor is of the formula (II):

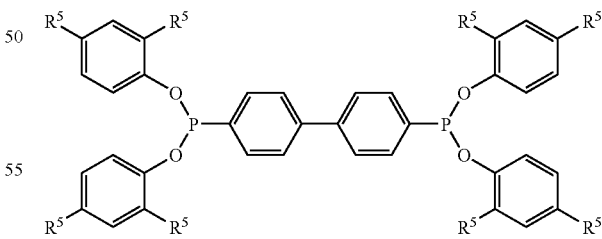

in which the radicals $R^5$, which are identical or different, are linear or branched alkyls having 1 to 12 C atoms.

14. The process according to claim 13, wherein the radicals $R^5$ are identical linear or branched alkyls having 4 to 12 C atoms.

15. The process according to claim 14, wherein the radicals $R^5$ are t-Bu radicals.

16. The process according to claim 1, wherein the inhibitor is of the formula (IX):

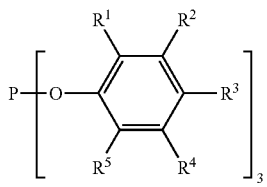

in which $R^1$, $R^2$, $R^3$, $R^4$ and $R^5$, which are identical or different, represent H, a linear or branched aliphatic radical, saturated, of formula $C_nH_{2n+1}$, or unsaturated, of formula $C_mH_{2m-1}$, or a radical of formula $C_nF_{2n+1}$, with n=1 to 15 and m=3 to 15, it not being possible for all of these radicals together to represent H.

17. The process according to claim 1, wherein the inhibitor is:

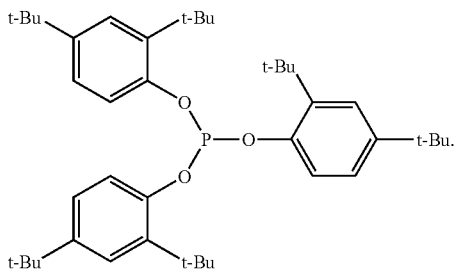

18. A process for preparing a catalyst additive or assembly comprising a metallic hydrosilylation catalyst and an organophosphorus compound which inhibits the catalytic action of the catalyst at room temperature, said process comprising adding said organophosphorus compound to a silicone gum or oil and dispersing said organophosphorus compound in said silicone gum or oil at a temperature greater than the melting temperature or softening temperature of said organophosphorus compound, and then mixing said catalyst into the composition thus obtained,
wherein the composition formed from the silicone gum or oil and the organophosphorus inhibitor is cooled prior to mixing said composition with said catalyst.

19. The process according to claim 18, wherein the composition is cooled at room temperature prior to mixing with said catalyst.

20. The process according to claim 18, wherein the catalyst is a platinum/unsaturated silane or platinum/unsaturated siloxane solution.

21. The process according to claim 20, wherein the catalyst is a platinum/vinylsiloxane solution.

22. The process according to claim 21, wherein the catalyst is a Karstedt solution.

23. The process according to claim 18, wherein the organophosphorus compound is selected from organophosphorus compounds of formula (I):

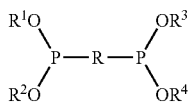

in which:
R, $R^1$, $R^2$, $R^3$ and $R^4$, which are identical or different, represent a linear, branched or cyclic alkyl radical or an aryl or alkylaryl radical which is substituted or unsubstituted;

or wherein the organophosphorus compound is of the formula (VIII) $P(OR)_3$ in which R is an alkylaryl radical having 7 to 31 carbon atoms.

24. The process according to claim 23, wherein the organophosphorus compound has formula (I) wherein each linear or branched alkyl radical has 2 to 30 carbon (C) atoms.

25. The process according to claim 24, wherein each linear or branched alkyl radical has 2 to 12 C atoms.

26. The process according to claim 23, wherein the organophosphorus compound has formula (I) wherein each cyclic alkyl radical has one or more rings having 4 to 14 C atoms.

27. The process according to claim 26, wherein each cyclic alkyl radical has 1 or 2 rings having 5 to 8 C atoms.

28. The process according to claim 23, wherein each aryl or alkylaryl radical has one or more fused or unfused aromatic rings having 4 to 14 C atoms, which is or are optionally substituted by 1 or more linear or branched alkyl(s) having 1 to 12 C atoms.

29. The process according to claim 28, wherein each aryl or aralkyl radical has 1 or 2 fused or unfused aromatic rings having 6 to 8 C atoms which is or are optionally substituted by 1 or more linear or branched alkyl(s) having 1 to 12 C atoms.

30. The process according to claim 29, wherein each aryl radical is a substituted phenyl radical.

31. The process according to claim 23, wherein the organophosphorus compound is of the following formula (IX):

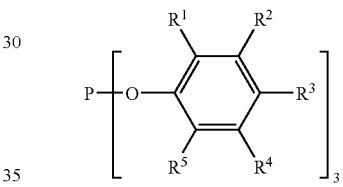

in which $R^1$, $R^2$, $R^3$, $R^4$ and $R^5$, which are identical or different, represent H, a linear or branched aliphatic radical, saturated, of formula $C_nH_{2n+1}$, or unsaturated, of formula $C_mH_{2m-1}$, or a radical of formula $C_nF_{2n+1}$, with n=1 to 15 and m=3 to 15, it not being possible for all of these radicals together to represent H.

32. The process according to claim 23, wherein the organophosphorus compound is of the following formula (X):

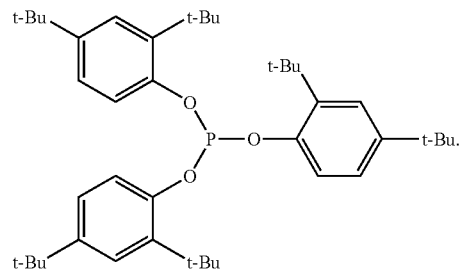

33. A catalyst additive or assembly comprising a hydrosilylation catalyst and an organophosphorus compound which inhibits the catalytic action of the catalyst at room temperature, obtained by the process according to claim 18.

34. The catalyst additive or assembly comprising a hydrosilylation catalyst and an organophosphorus compound which inhibits the catalytic action of the catalyst at room temperature, wherein the organophosphorus compound is of the formula (II):

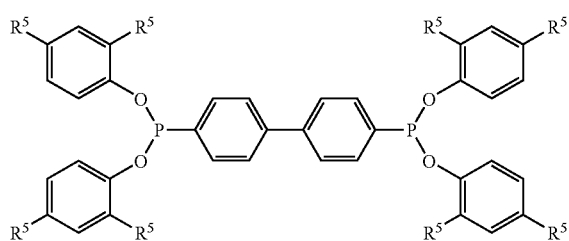

in which the radicals R⁵, which are identical or different, are linear or branched alkyls having 1 to 12 C atoms.

35. The catalyst additive or assembly according to claim 34, wherein the radicals R⁵ are identical linear or branched alkyls having 4 to 12 C atoms.

36. The catalyst additive or assembly comprising a hydrosilylation catalyst and an organophosphorus compound which inhibits the catalytic action of the catalyst at room temperature, wherein the organophosphorus compound is of the formula (III):

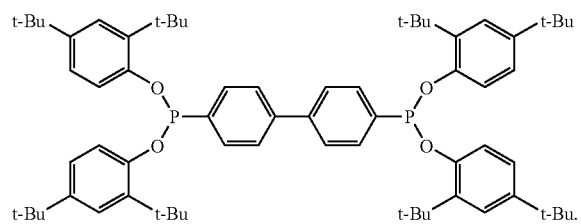

37. A catalyst additive or assembly comprising a hydrosilylation catalyst and an organophosphorus compound which inhibits the catalytic action of the catalyst at room temperature, comprising the following chemical species:

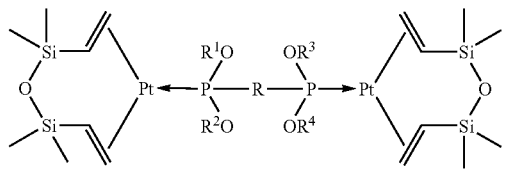

in which the radicals R⁵, which are identical or different, are linear or branched alkyls having 1 to 12 C atoms.

38. The catalyst additive or assembly according to claim 37, wherein the radicals R⁵ are identical linear or branched alkyls having 4 to 12 C atoms.

39. A catalyst additive or assembly comprising a hydrosilylation catalyst and an organophosphorus compound which inhibits the catalytic action of the catalyst at room temperature, comprising the following chemical species:

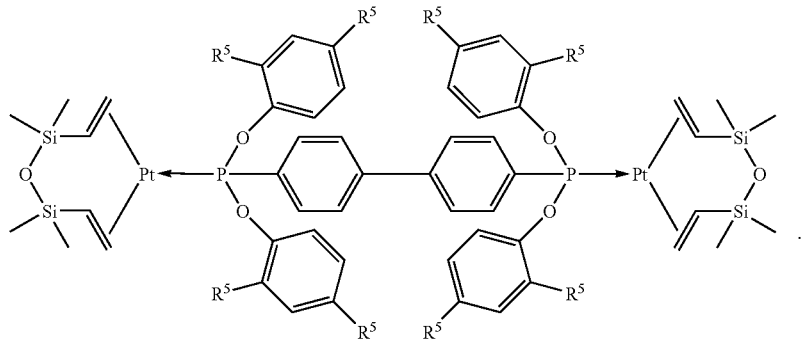

\* \* \* \* \*